United States Patent
Abenaim et al.

(10) Patent No.: US 9,348,055 B2
(45) Date of Patent: May 24, 2016

(54) SECURITY SCANNER

(75) Inventors: Daniel Abenaim, Lynnfield, MA (US); Charles H. Shaughnessy, Peabody, MA (US)

(73) Assignee: Analogic Corporation, Peabody, MA (US)

( * ) Notice: Subject to any disclaimer, the term of this patent is extended or adjusted under 35 U.S.C. 154(b) by 136 days.

(21) Appl. No.: 14/125,347

(22) PCT Filed: Jun. 14, 2011

(86) PCT No.: PCT/US2011/040253
§ 371 (c)(1),
(2), (4) Date: Dec. 11, 2013

(87) PCT Pub. No.: WO2012/173597
PCT Pub. Date: Dec. 20, 2012

(65) Prior Publication Data
US 2014/0126694 A1    May 8, 2014

(51) Int. Cl.
*G01N 23/00* (2006.01)
*G01V 5/00* (2006.01)
*G01N 23/04* (2006.01)

(52) U.S. Cl.
CPC ............ *G01V 5/0016* (2013.01); *G01N 23/046* (2013.01); *G01V 5/0008* (2013.01)

(58) Field of Classification Search
CPC ..... G01N 23/04; G01N 23/083; G01N 23/10; G01N 2223/308; G01N 2223/316; G01N 2223/33; G01N 2223/3301; G01N 2223/3308; G01N 2223/626; G01N 2223/639; G01N 2223/643; G01V 5/0008; G01V 5/0016; G01V 5/0066; H05G 1/02
See application file for complete search history.

(56) References Cited

U.S. PATENT DOCUMENTS

| | | | | | |
|---|---|---|---|---|---|
| 4,398,302 | A | * | 8/1983 | Pfeiler | 378/146 |
| 4,686,695 | A | * | 8/1987 | Macovski | 378/146 |
| 4,763,345 | A | * | 8/1988 | Barbaric | A61B 6/06 378/145 |
| 5,046,003 | A | * | 9/1991 | Crawford | 378/15 |

(Continued)

FOREIGN PATENT DOCUMENTS

| | | |
|---|---|---|
| JP | 2008-026334 | 2/2008 |
| WO | 2004-054329 A2 | 6/2004 |
| WO | 2006138529 A2 | 12/2006 |

OTHER PUBLICATIONS

JP2014-515792 First Japanese Office Action dated Feb. 10, 2015.

(Continued)

*Primary Examiner* — Thomas R Artman
(74) *Attorney, Agent, or Firm* — Anthony M. Del Zoppo, III; Driggs, Hogg, Daugherty & Del Zoppo, Co. LPA

(57) ABSTRACT

A scanner (200) includes a radiation source (202) that emits radiation that traverses a scanning region and a detector array (204), including a line of detectors (302), that detects radiation traversing the scanning region, wherein the radiation source and the detector array are located on opposing sides of the scanning region. The scanner further includes a mover (208) configured to move an object through the scanning region when scanning the object. The line of detectors (302) is configured to move in a plane, which is substantially parallel to the scanning region, in coordination with the mover moving the object, thereby creating a plane of detection for scanning the object.

23 Claims, 16 Drawing Sheets

(56) References Cited

U.S. PATENT DOCUMENTS

| | | | |
|---|---|---|---|
| 5,717,732 A * | 2/1998 | Tam .................................. 378/4 |
| 7,062,011 B1 | 6/2006 | Tybinkowski et al. |
| 7,236,572 B2 * | 6/2007 | Maschke ....................... 378/146 |
| 7,342,993 B2 * | 3/2008 | Besson .................. A61B 6/025 250/370.1 |
| 7,404,673 B2 * | 7/2008 | Hornig ................. A61B 6/4225 348/E5.086 |
| 7,539,284 B2 * | 5/2009 | Besson .................. A61B 6/032 378/147 |
| 7,734,016 B2 * | 6/2010 | Watanabe .............. G03B 42/02 378/117 |
| 2002/0176534 A1 | 11/2002 | Meder |
| 2007/0140412 A1 * | 6/2007 | Holt ................................. 378/8 |
| 2011/0206179 A1 * | 8/2011 | Bendahan ............ G01V 5/0016 378/19 |

OTHER PUBLICATIONS

International search report for PCT/IB2011/040253 published as WO 2012/173597 A1.

W. Mauderli, et al., A Computerized Rotating Laminar Radionuclide Camera, The Journal of Nuclear Medicine, 1979, 341-344, vol. 20, No. 4, University of Florida, Gainesville, Florida, Galileo-Electrooptics, Sturbridge, MA and Radiation Monitoring Devices, Watertown, MA.

Westminster International Ltd., Pallet & Cargo Scanners—Security from Westminster International, Oxfordshire, United Kingdom, 2009, one page.

* cited by examiner

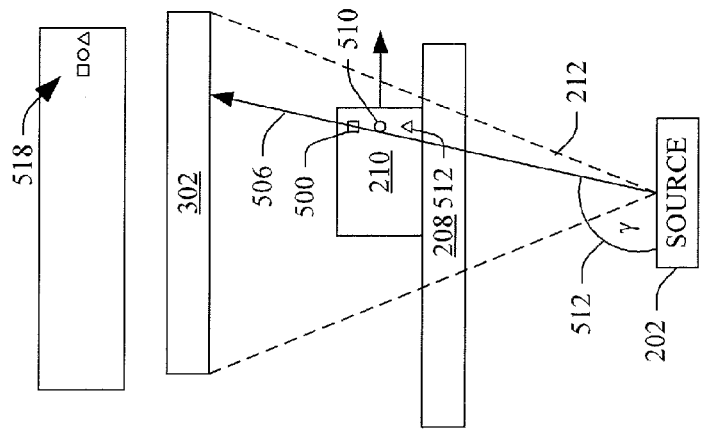
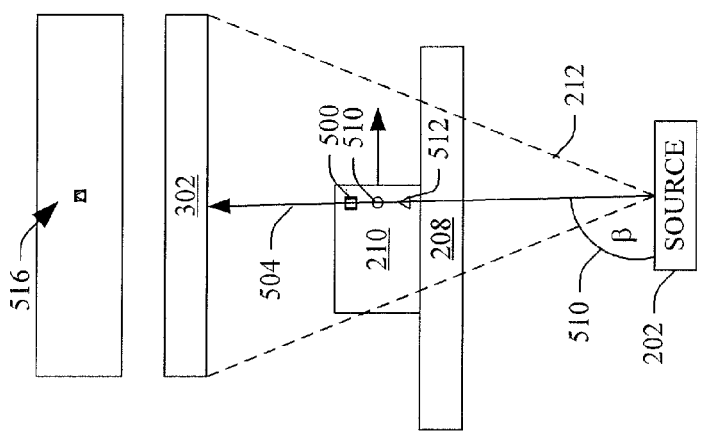
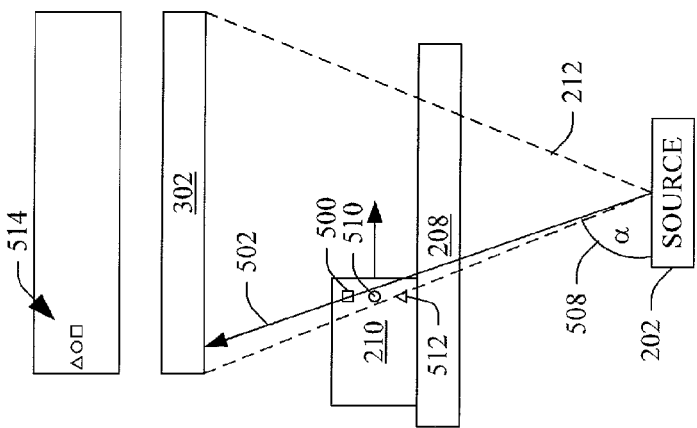

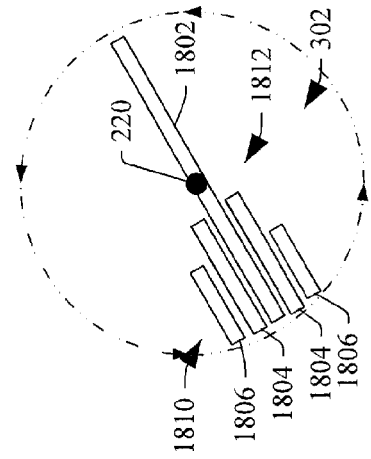
FIGURE 16
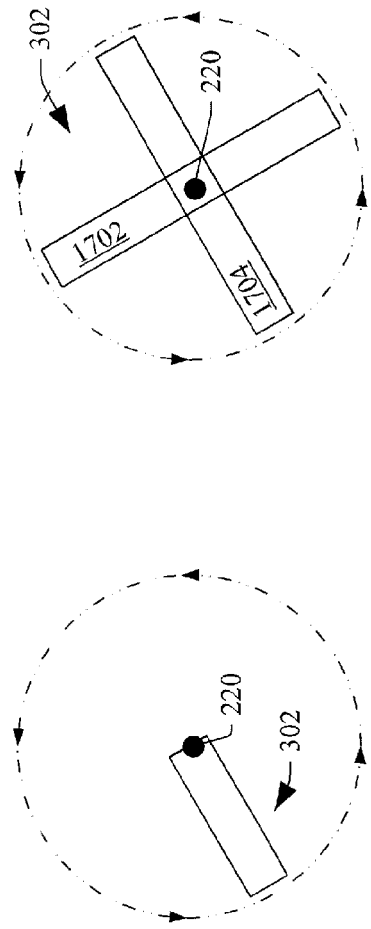
FIGURE 17
FIGURE 18
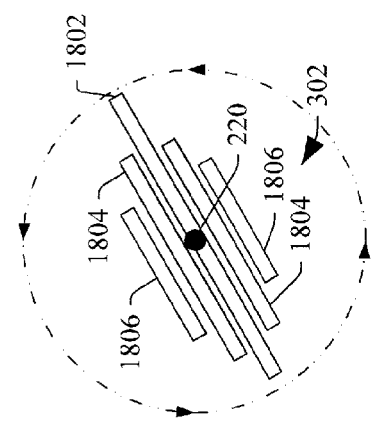
FIGURE 19
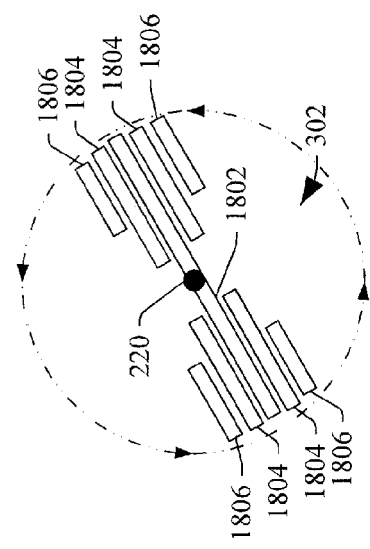
FIGURE 20
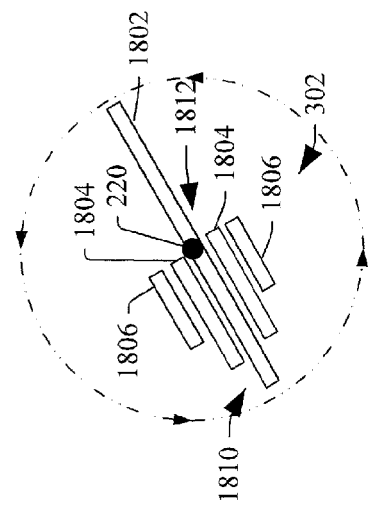
FIGURE 21

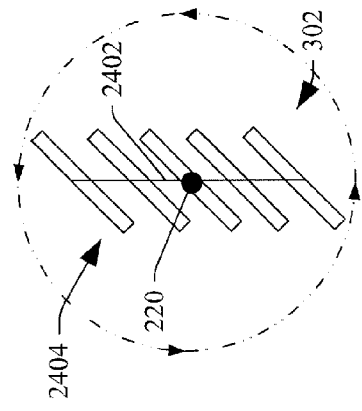
FIGURE 24
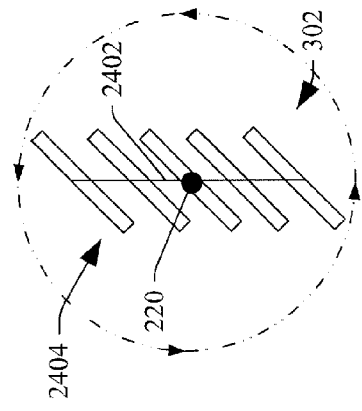
FIGURE 23
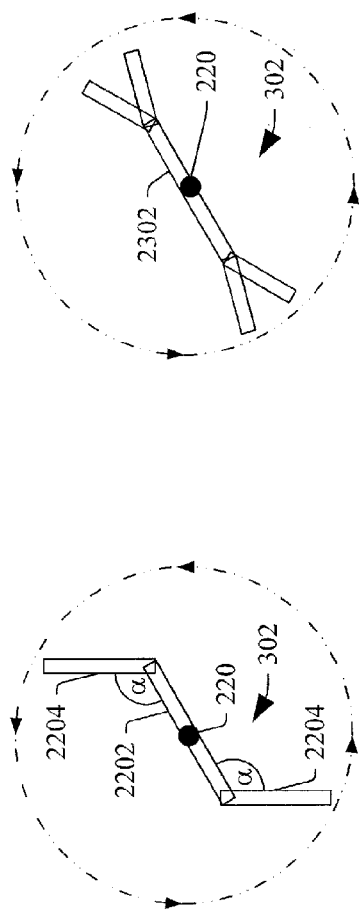
FIGURE 22
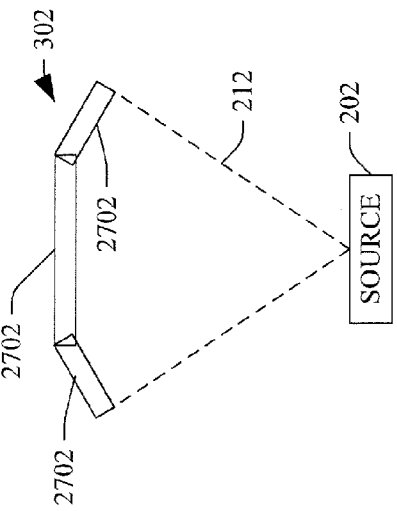
FIGURE 27
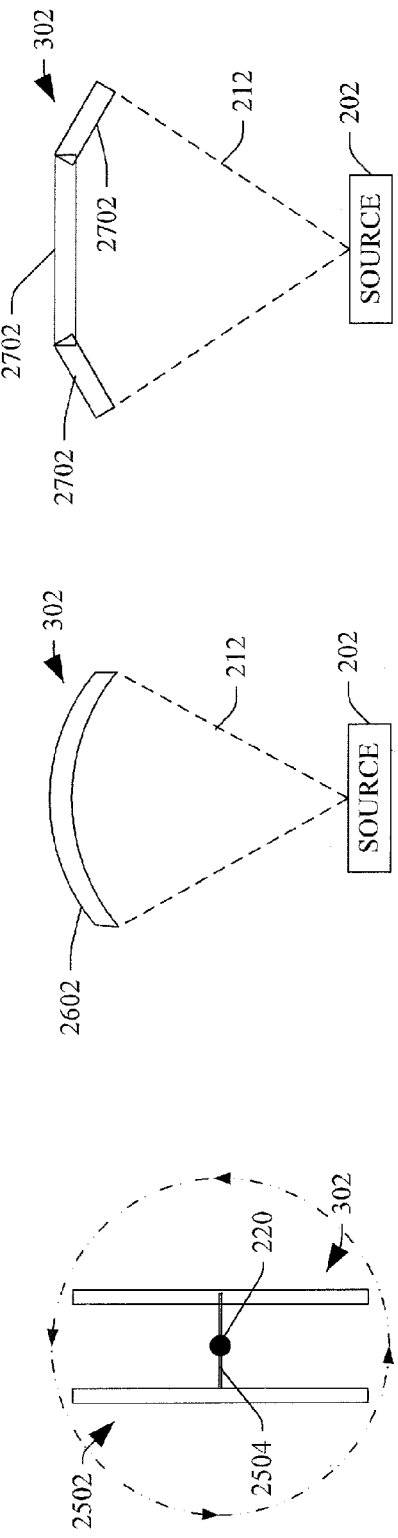
FIGURE 26
FIGURE 25

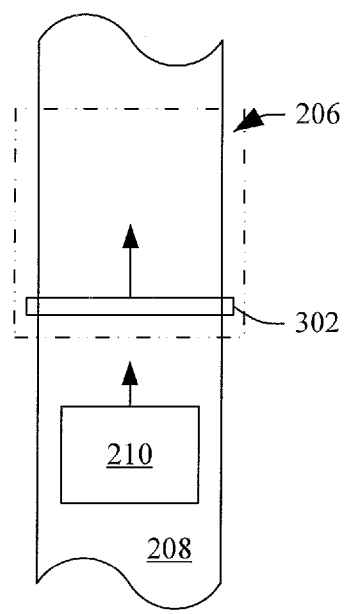
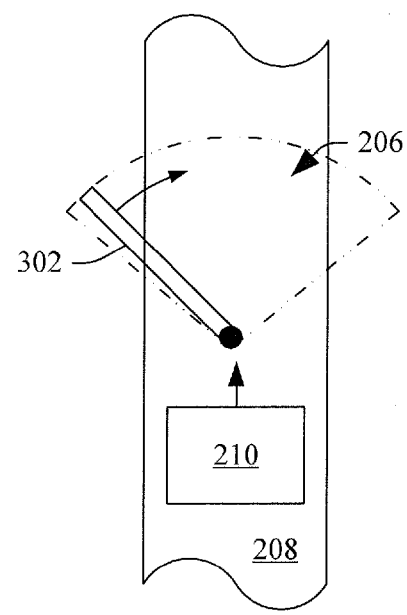
FIGURE 28
FIGURE 29
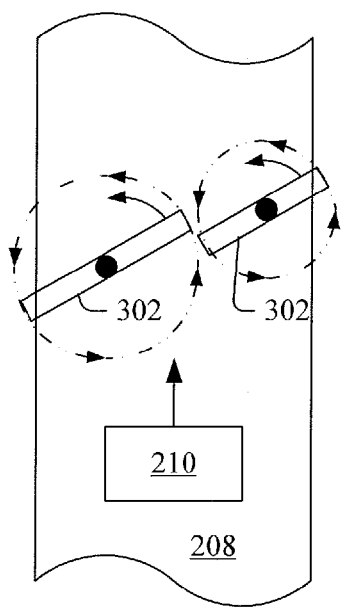
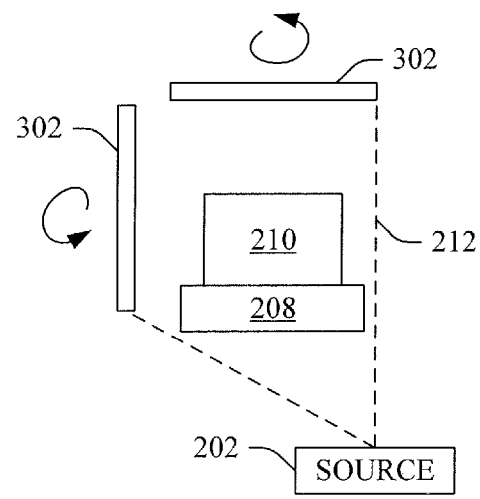
FIGURE 30
FIGURE 31

SECURITY SCANNER

RELATED APPLICATION

This application is a national filing of PCT application Serial No. PCT/US2011/040253, filed Jun. 14, 2011, published as WO2012/173597 on Dec. 20, 2012. This application claims priority to PCT application Serial No. PCT/US2011/040253, published as WO2012/173597 on Dec. 20, 2012.

TECHNICAL FIELD

The following generally relates to imaging and finds particular application to a security scanner. However, the following is also amenable to other applications.

BACKGROUND

Every day, large volumes of people travel by way of aircraft, making the airlines (the airport and/or aircrafts) attractive targets for terrorism, including aircraft hijacking and using hijacked aircraft as lethal weapons. Airport security provides a defense against such terrorism by attempting to stop would-be attackers from bringing weapons, explosive materials, and/or other potentially lethal contraband into the airport. Lines of defense have included Sky Marshals, metal detectors, luggage scanners, puffer machines (which can detect traces of compounds of interest), explosive detection machines (which detect volatile compounds given off from explosives using gas chromatography), and backscatter x-ray scanners that detect hidden weapons and explosives on passengers. Carry on luggage scanners have included x-ray based imaging systems which allow for "looking inside" luggage without opening the luggage. Computed tomography based scanners generate three dimensional 3D information indicative of the contents of the luggage. Unfortunately, such scanners tend to be expensive and have been primarily used to screen checked in luggage.

At security check points, x-ray line scanners typically are utilized to scan carry on luggage. FIG. 1 schematically illustrates an example line scanner 100, which includes a conveyor 102 that moves luggage 104 through a scanning region 106 located between an x-ray source 108 and a line of detectors 110 as the x-ray source 108 emits radiation 112 that traverses the scanning region 106 and illuminates the detectors 110. The line of detectors 110 generates signals indicative of the detected radiation, and the signals are processed to generate a single 2D projection image of the scanned region. However, 2D projection images do not provide volume information and, therefore, threats may be able to be hidden behind dense objects. Three dimensional (3D) data can be acquired using multiple detector line/x-ray source pairs located at different angles. Unfortunately, adding additional detector line/x-ray source pairs increases cost and consume additional space.

In view of at least the above, there is an unresolved need for other approaches for security scanners.

SUMMARY

Aspects of the application address the above matters, and others.

In one aspect, a scanner includes a radiation source that emits radiation that traverses a scanning region and a detector array, including a line of detectors that detects radiation traversing the scanning region, wherein the radiation source and the detector array are located on opposing sides of the scanning region. The scanner further includes a mover configured to move an object through the scanning region when scanning the object. The line of detectors is configured to move in a plane, which is substantially parallel to the scanning region, in coordination with the mover moving the object, thereby creating a plane of detection for scanning the object.

In another aspect, a method for scanning an object includes moving a line of detectors parallel to a scanning region so as to create a plane of detection for scanning the object in the scanning region, moving the object through the scanning region, producing radiation that traverses the scanning region and the object moving there through, detecting the radiation traversing the scanning region and the object with the plane of detection and generating a signal indicative thereof.

In another aspect, a computer readable storage medium with computer executable instructions embedded thereon, which, when executed by a processor, cause the processor to: move a line of detectors parallel to a scanning region so as to create a plane of detection for scanning an object in the scanning region, move a mover to move the object through the scanning region, activate a source to produce radiation that traverses the scanning region and the object moving there through, activate the line of detectors to detect the radiation traversing the scanning region and the object with the plane of detection and generate a signal indicative thereof, and generate three dimensional data of the object, including an interior of the object, based on the signal.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which:

FIGS. 5, 6 and 7 schematically illustrate obtaining multiple views for each voxel while rotating the line of detectors and moving the object through the scanning region;

FIGS. 16, 17, 18, 19, 20, 21, 22, 23, 24, 25, 26 and 27 schematically illustrate example variations of the line of detectors;

FIG. 28 schematically illustrates an example line scanner in which the line of detectors is configured to translate to create a plane of detection;

FIG. 29 schematically illustrates an example line scanner in which the line of detectors is configured to pivot to create a plane of detection;

FIG. 30 schematically illustrates an embodiment in which the system includes multiple lines of detectors that move in a same plane.

FIG. 31 schematically illustrates an embodiment in which the system includes multiple lines of detectors that move in different planes.

DETAILED DESCRIPTION

The following relates to a low cost x-ray imaging system suitable for, amongst other uses, screening carry on bags at airport check points. Generally, the system includes a line detectors, which is configured to rotate, translate, pivot and/or otherwise move to create a plane of detection, which is used to acquire data that can be reconstructed to generate three dimensional (3D) volume data indicative of a scanned bag, which allows for discrimination of one or more objects inside the bag.

Figure 1:
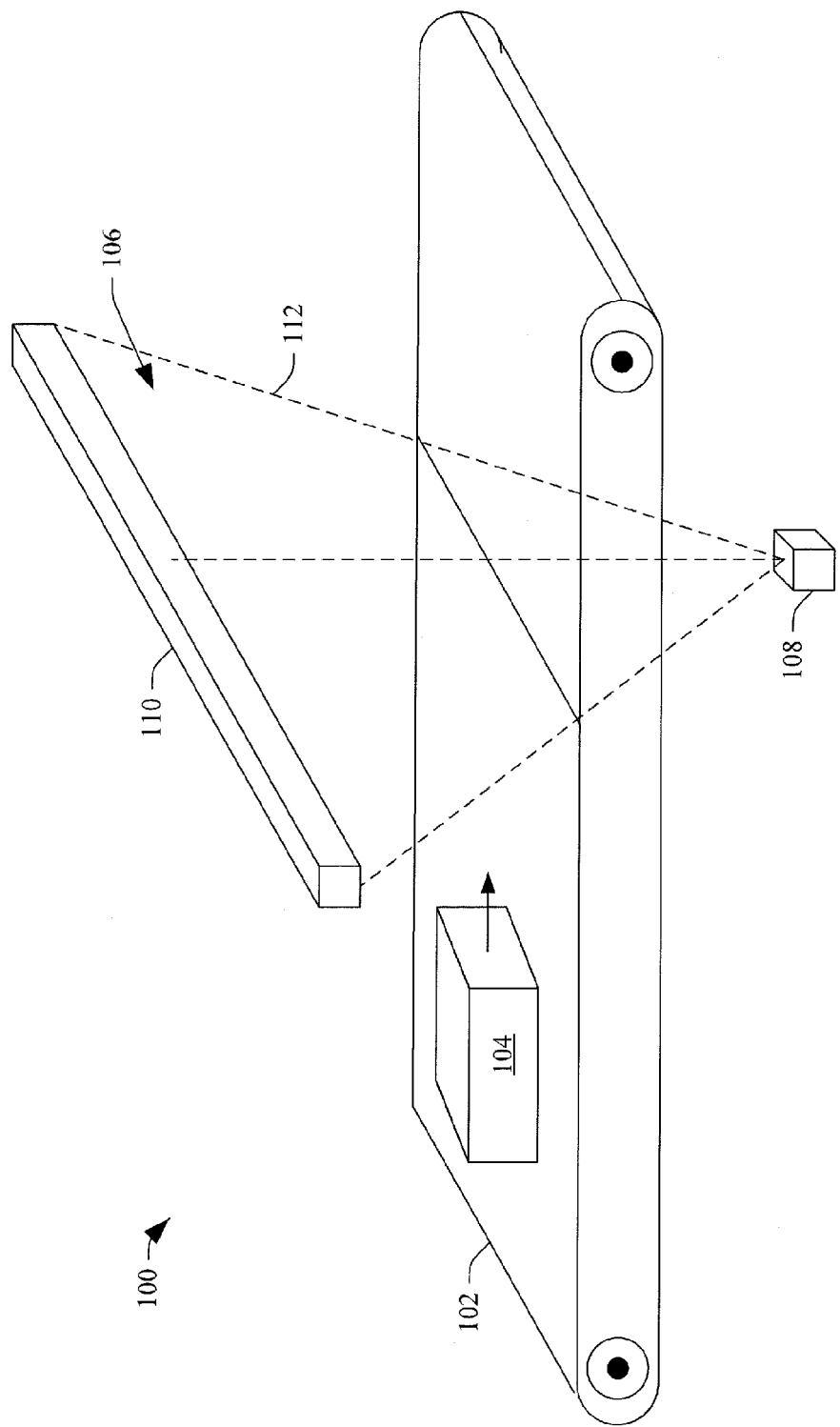
FIG. 1 schematically illustrates an example prior art line scanner.
Figure 2:
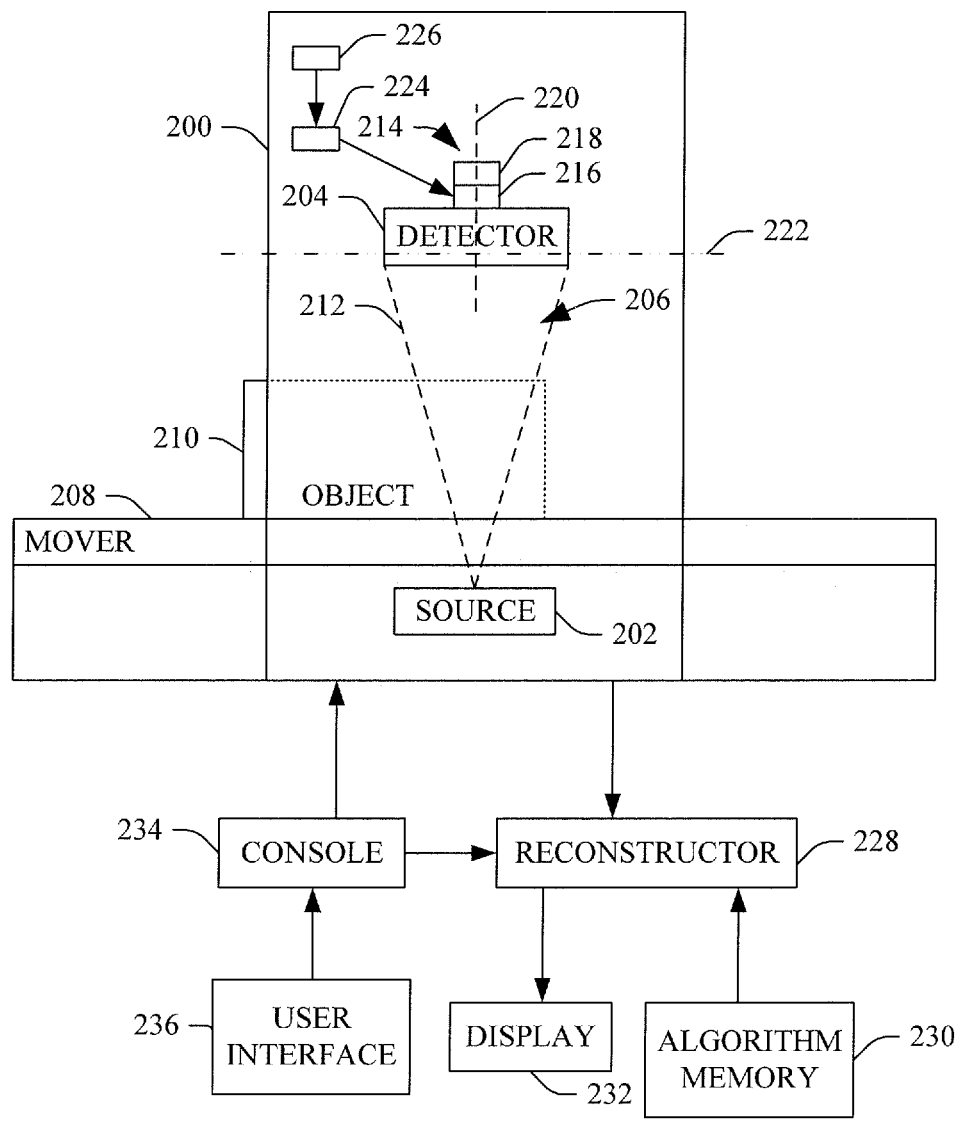
FIG. 2 schematically illustrate an example line scanner in which the line of detectors is configured to move to create a plane of detection.

FIG. 2 illustrates a scanner 200 that includes a radiation source 202, such as an x-ray tube, and a radiation sensitive detector 204, which are located on opposite sides of a scanning region 206, and a mover 208 that is configured to support and move an object 210 in the scanning region 206 for scanning the object 210.

The source 202 emits radiation 212 that traverses the scanning region 206 (and an object therein, such as the object 210, which is shown partially in the scanning region 206 in the illustrated embodiment) and illuminates the detector 204. Suitable sources include single energy sources and multiple energy sources, which are configured to switch between emission spectrums (e.g., between two or more kVps) during scanning via voltage switching and/or other approach. In yet another embodiment, the system 200 includes two or more of the sources 202.

The detector 204 detects radiation traversing the scanning region 206 and generates a signal indicative thereof. The detector 204 may include conventional and/or energy resolving detectors. The detector 204 is rotatably mounted via a coupling 214 (e.g., a bearing or the like). The coupling 214 has a rotating portion 216 and a stationary portion 218. The detector 204 is affixed to the rotating portion 216 and rotates in coordination therewith about a rotation axis 220 in a plane 222, which is parallel to the scanning region 206.

A motor 224 rotates the rotating portion 216 and hence the detector 204. A motor controller 226 drives a motor 224.

As described in greater detail below, in one instance, the detector 204 includes a single line or row of detectors, and the motor controller 226 drives the motor 224 to rotate the rotating portion 216 and hence the detector 204 and the line of detectors such that the line of detectors creates a plane of detection for the scanning region 206, allowing for acquiring projections for a voxel in the scanning region 206 from a plurality of different angles.

A reconstructor 228 reconstructs the signals and generates two dimensional (2D) and/or three dimensional (3D) data representing the scanned object 210. Algorithm memory 230 includes one or more algorithms, such as 2D and 3D algorithms, conventional, iterative, spectral, etc. algorithms, and/or other algorithms, any of which can be used by the reconstructor 228 to reconstruct the signal. A display 232 can be used to visually present the reconstructed data in human readable format.

A console 234, such as a general purpose computer, controls various components of the system 200. A user interface 236 includes various input devices (e.g., a keyboard, a key pad, a mouse, a touch pad, etc.) that can be used by a user of the system 200 to interact with the console 234 and control the system 200. Such interaction may include initiating scanning, manipulating (e.g., zooming, panning, etc.) an image displayed on the display 232, etc.

FIGS. 3A, 3B, 3C, 4, 5, 6, 7, 8, 9 and 10 schematically illustrate a non-limiting embodiment of the system 200. It is to be understood that this example if provided for explanatory purposes and is not limiting; other embodiments are also contemplated herein.

Figure 3C:
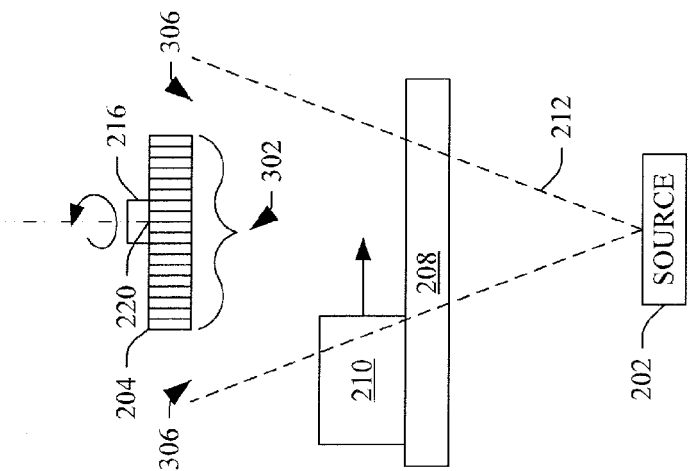
FIGS. 3A, 3B, 3C and 4 schematically illustrate an example line scanner in which the line of detectors is configured to rotate to create the plane of detection.
Figure 3B:
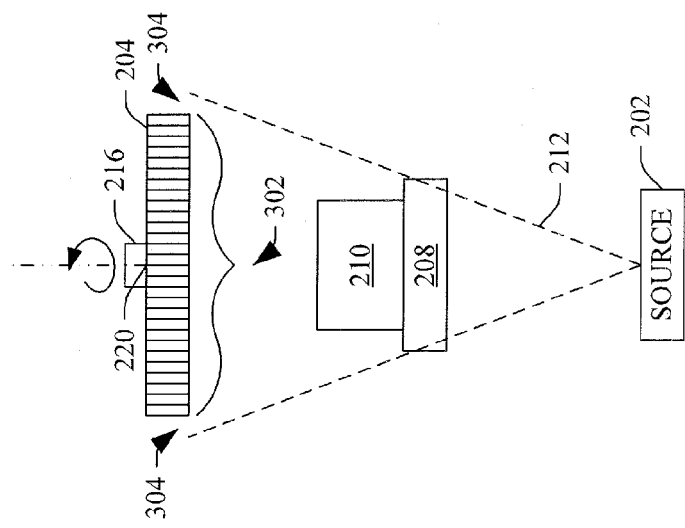
Figure 3A:
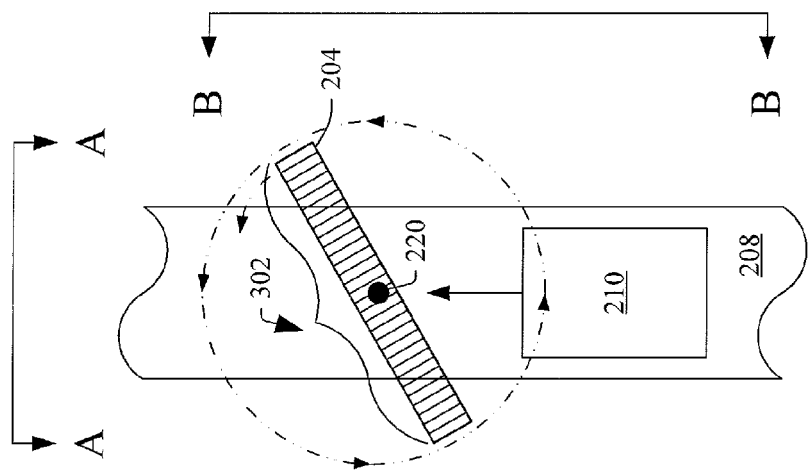

FIGS. 3A, 3B and 3C schematically illustrate a non-limiting example of the detector 204. FIG. 3A illustrates a top down view looking down into the system 200 in a direction from the detector 204 to the source 202 (which is not visible). FIG. 3B illustrates a view along line A-A of FIG. 3A, and FIG. 3C illustrates a side view along line B-B of FIG. 3A. In all three of 3A, 3B and 3C, the detector 204 is located at the same relative angular rotational position.

In FIGS. 3A, 3B and 3C, the detector 204 includes a single linear or straight row or line of detectors 302, which is generally symmetric about the rotation axis 220 in that a length and number of detectors extending in opposing directions from the rotation axis 220 is approximately the same. The line of detectors 302 is shown rotating in a counter clockwise direction through the same angle in all three figures with the mover 208 moving the object 210. The line of detectors 302 could alternatively rotate in a clockwise direction, and the illustrated direction of the mover 208 is not limiting.

Figure 4:
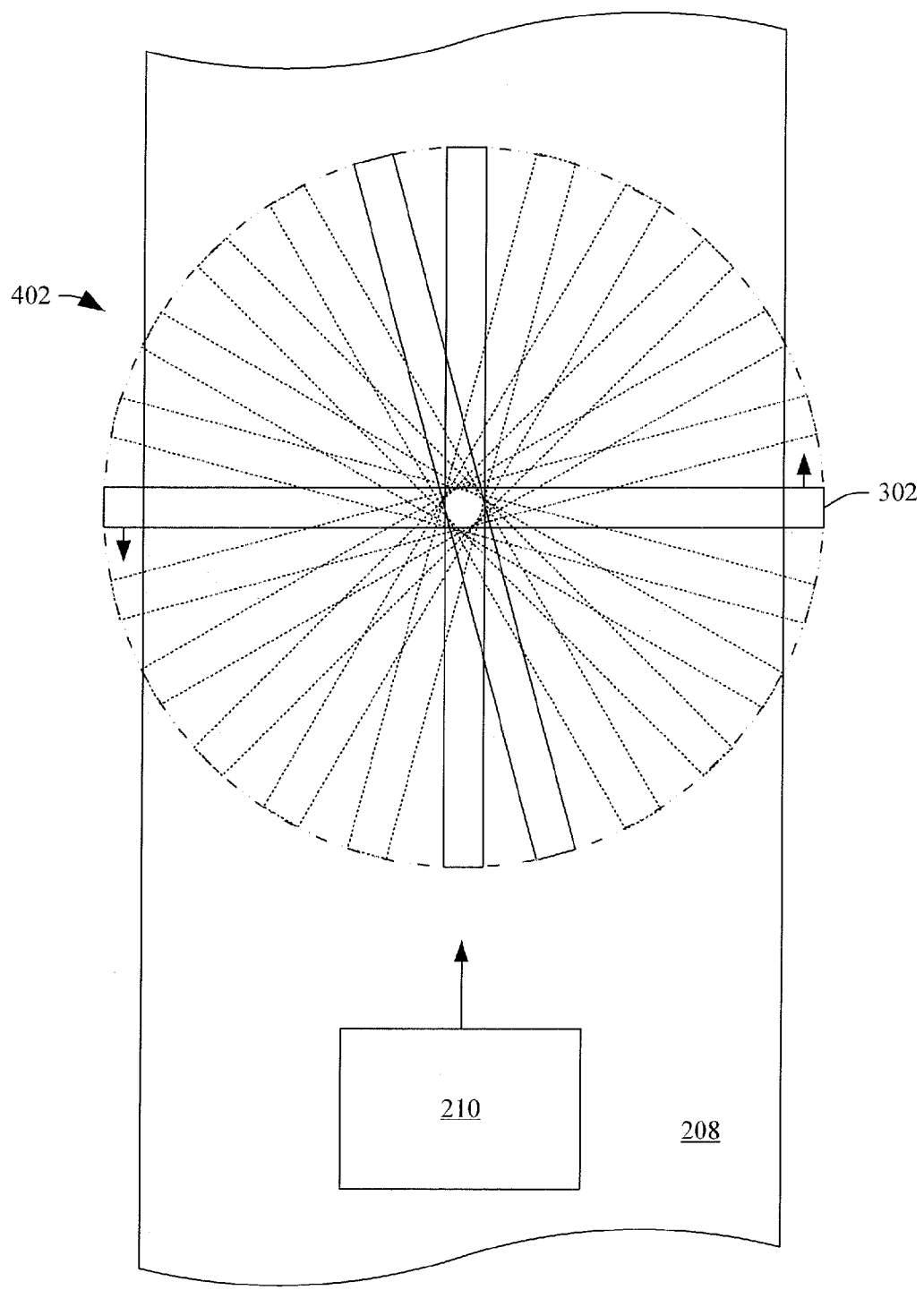

As shown in FIG. 4, the line of detectors 302 can be rotated to create or emulate a plane of detection 402 for the scanning region 206, with greater sampling density nearer to the axis of rotation. In this instance, the line of detectors can be rotated at sufficient speed, relative to the moving object, so that each voxel in the scanning region 206 can be sampled a number of times from different angles at different time samples. In one non-limiting instance, the line of detectors 302 rotates a full 360 degrees for every one or more centimeters of movement of the object.

The above is shown in FIGS. 5, 6 and 7 in connection with a single voxel 500. In FIG. 5, a first ray 502 traversing at a first angle 508 traverses the voxel 500. In FIG. 6, a second ray 504 traversing at a second angle 510 traverses the voxel 500. In FIG. 7, a third ray 506 traversing at a third angle 512 traverses the voxel 500. FIGS. 5, 6 and 7 also show the voxel 500 in relation to two other voxels 510 and 512, which are located in the object at different elevations along the y-axis direction and at a same x-axis location with respect to the voxel 500. In FIGS. 5, 6 and 7, 514, 516 and 518 respectively show how the voxels 500, 510 and 512 are differentiated along the line of detectors 302 as the object 210 traversing in front of the line of detectors 302. Note at 516, the voxels 500, 512 and 514 are concurrently seen by the same detector of the line of detectors 302. In FIGS. 5, 6 and 7, the line of detector 302 is at the same angular position, but does not have to be.

Figure 8:
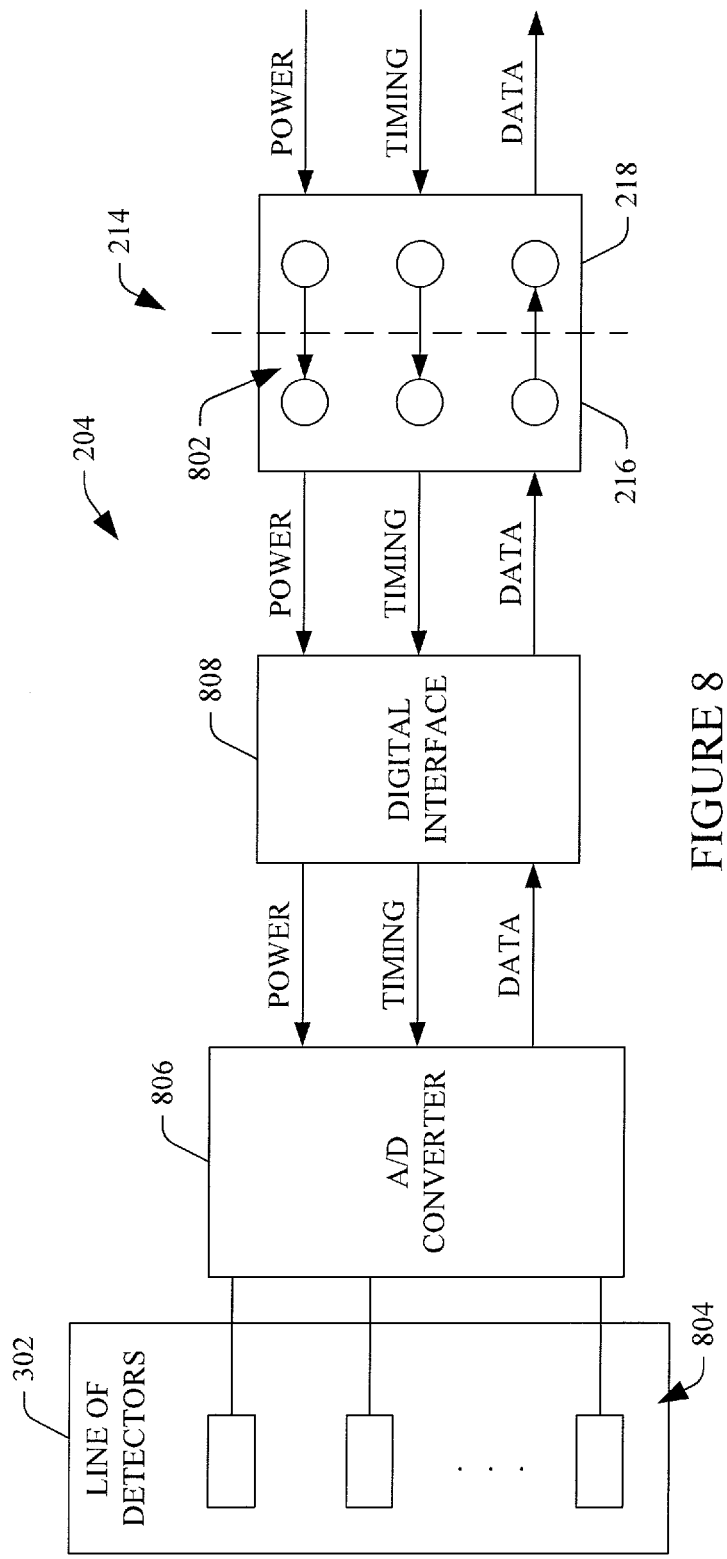
FIG. 8 schematically illustrates example electronics for transferring power, timing, data, etc. signals between the rotating detector and the system.

FIG. 8 shows example electronics for transferring data, power, timing signals, etc. through the coupling 214. In this example, the coupling 214 includes a slip ring 802 or other electrical connection which can be used to transfer data, power, timing signals, etc. between rotating and stationary portions. In this example, analog output of the detector elements 804 are processed by an analog to digital (A/D) converter 806, and the resulting digital output is transferred to the slip ring 802 via a digital inference 808 and to one or more components of the system 200.

Figure 9:
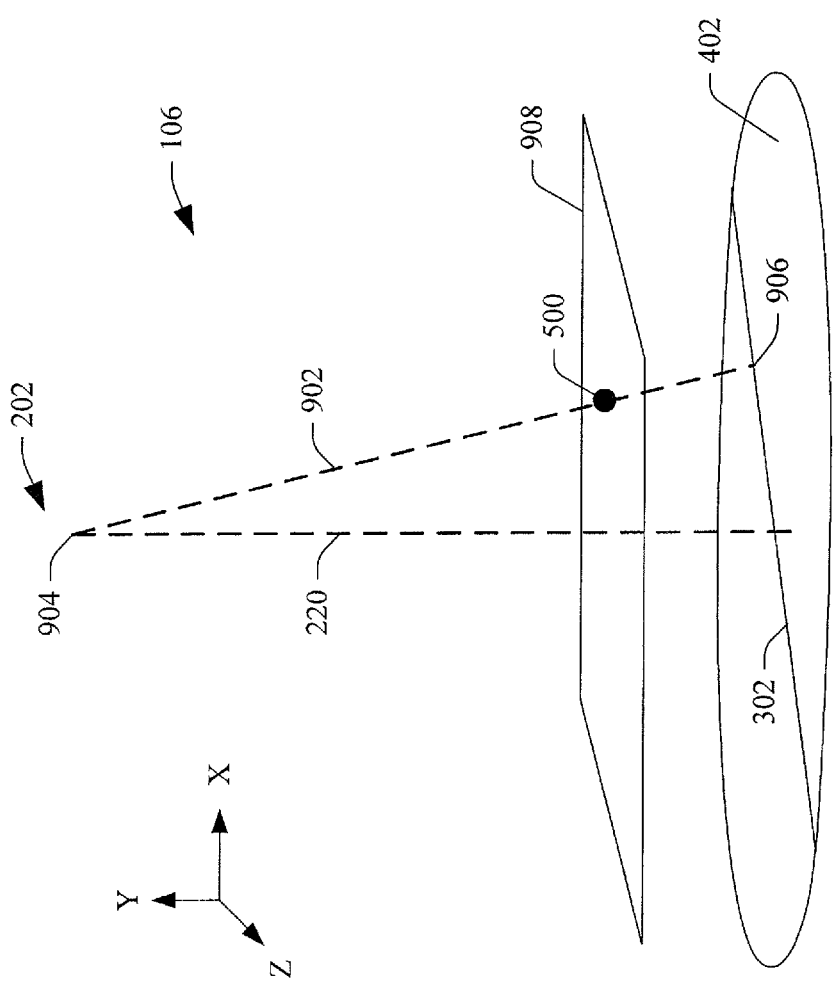
FIG. 9 illustrates example reconstruction technique for reconstructing a series of two dimensional images.

FIG. 9 illustrates an example reconstruction approach. In FIG. 9, the origin is arbitrary as the mover 208 motion is continuous, the z-axis runs along the direction of travel of the mover 208 (FIG. 2), the x-axis runs perpendicularly across the mover 208, with the axis of rotation 220 passing through the origin, and the y-axis is vertical, running along the rotation axis 220, having its origin at the surface of the mover 208.

The data generated by the line of detectors 302 includes a projection, for each detector element, collected at discrete time samples. As the mover 208 moves the object 210 in the scanning region 206, it is sampled a number of times as the line of detectors 302 rotates. Consequently, each voxel in the scanning region 206 is sampled from different angles as the object moves through the scanning region 206 while the line of detectors 302 rotates.

The reconstructor 228 reconstructs images by determining the intersection of each ray (e.g., a ray 902), from a focal spot 904 of the source 202, to a corresponding detector element (e.g., detector element 906) of the line of detectors 302, with a plane of interest 908 in the scanning region 206. In the illustrated instance, the plane 908 is substantially parallel to the mover 208. However, in other instances, the plane 908 may be any plane surface or any curved surface (e.g., which can be described analytically).

The image may be thought of as an array of bins of a particular size arranged in space. In the simplest case, the image consists of square elements (e.g., element 500), lying in a horizontal reconstruction plane 908 a given distance above the mover 208. The intersection of each ray (e.g., 902) with the reconstruction plane 908 can be expressed as a set of coordinates in the image. Each ray (e.g., 902) passes through only one pixel (e.g., 500) in the image. The projection length of each ray (the integral of $\mu$ times L along the path) is summed into the pixel (e.g., 500) it intersects. This process is repeated for all rays passing through the object 210. A series of contiguous or overlapping images may be generated from each scan, resulting in a three dimensional view of the article.

Prior to reconstructing the images, a series of physical and geometric corrections may be performed on the raw data. Such corrections may include, for example, calibrated correction of the sensor offset, gain, linearity and spectral response, and compensation for detector curvature.

Further, it will be noted that the sampling density of the rotating line of detectors 302 varies across the scanning region 206. As such, the features nearer the outer edges of the detector 204 are sampled less, relative to the features nearer the center of the detector 204. The result in the uncorrected image is that features positioned near the center of the imaging field of view appear brighter than those at the edges. One compensation approach can be used in which the raw projection data is weighted according to its distance from the center of the detector. A second compensation approach, which may be used in conjunction with the first, is to vary the sampling rate of the detector in proportion to the distance from the detector center.

Further, it will be noted that images reconstructed directly from projection data will be blurred. By filtering the projection data prior to image generation, using a ramp-shaped filter kernel which emphasizes high frequencies, the edges of objects will be maintained in the final image.

In another example, since the scan geometry does not provide a complete set of views of the object 210, there may be artifacts due to ghosting of features out of plane. An iterative reconstruction, in which a first image is reprojected, enhanced and reconstructed multiple times, can be performed on the data to reduce the ghosting effect.

Figure 10:
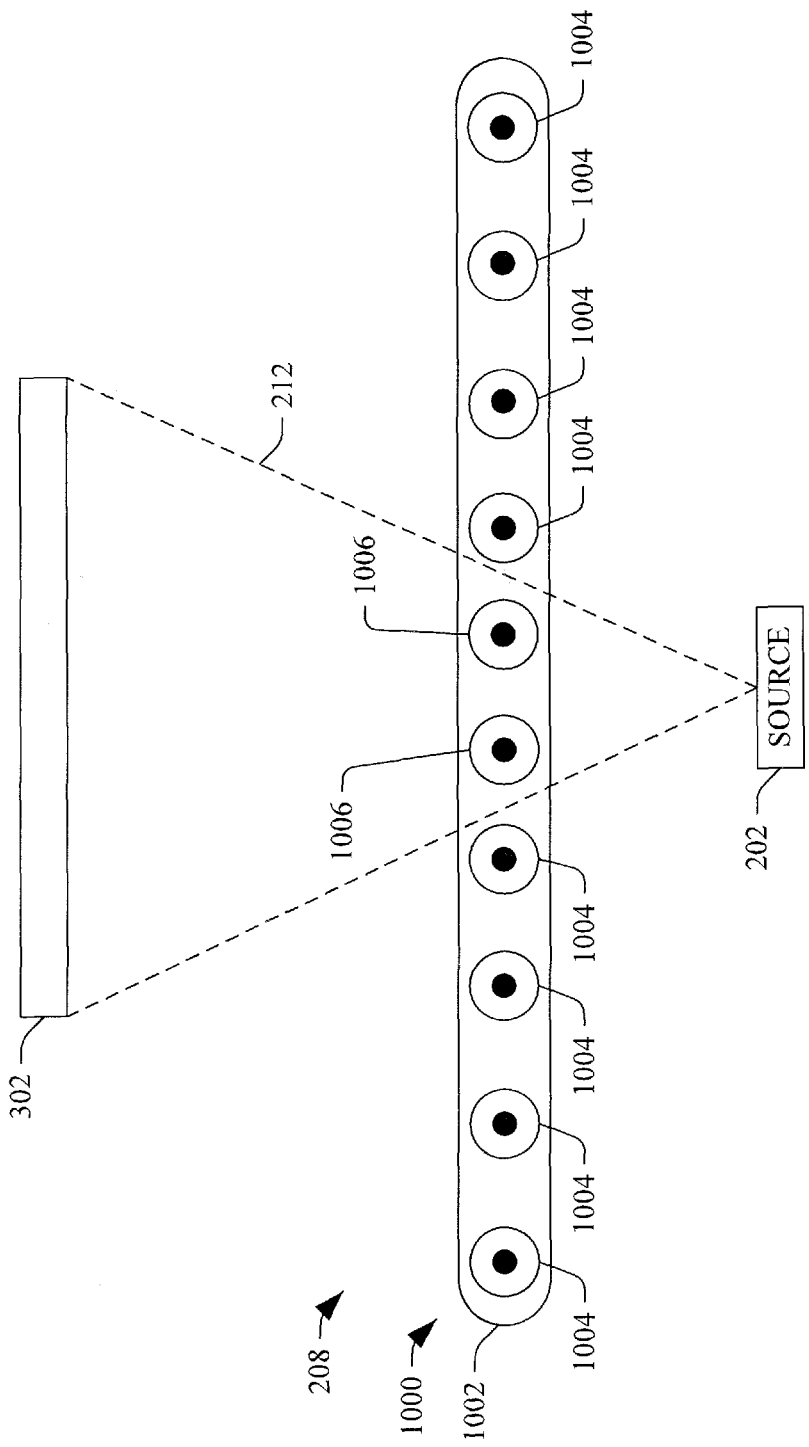
FIGS. 10, 14 and 15 schematically illustrate example movers of the scanner.

FIG. 10 schematically illustrates an example of the mover 208. In FIG. 10, the mover 208 includes a conveyor system 1000 with a belt 1002 and first and second sets of rollers 1004 and 1006, which rotate the belt 1002. The first set of rollers 1004 can be conventional rollers. The second set of rollers 1006, which are within the path of the radiation 212, includes radiation translucent material such as fiberglass tubes and/or other translucent material.

Variations are discussed.

Figure 12:
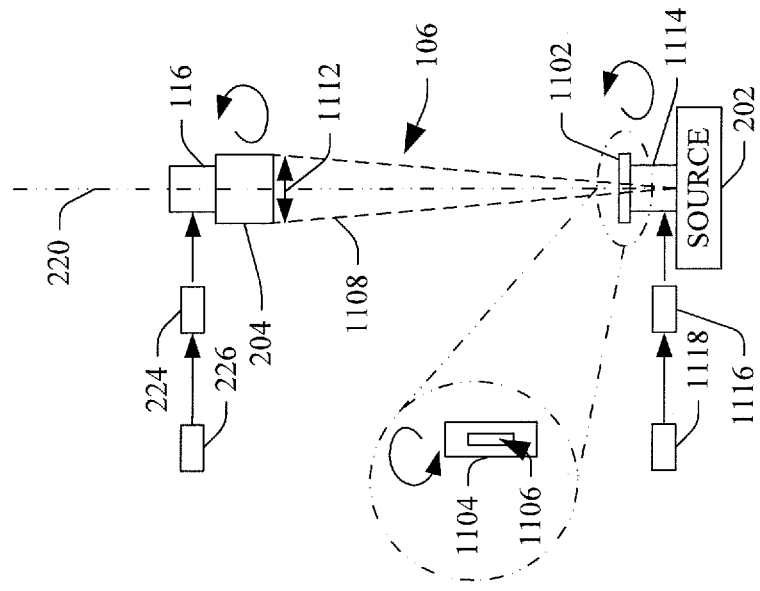
FIGS. 11, 12 and 13 schematically illustrate an example of the scanner with a source collimator.
Figure 11:
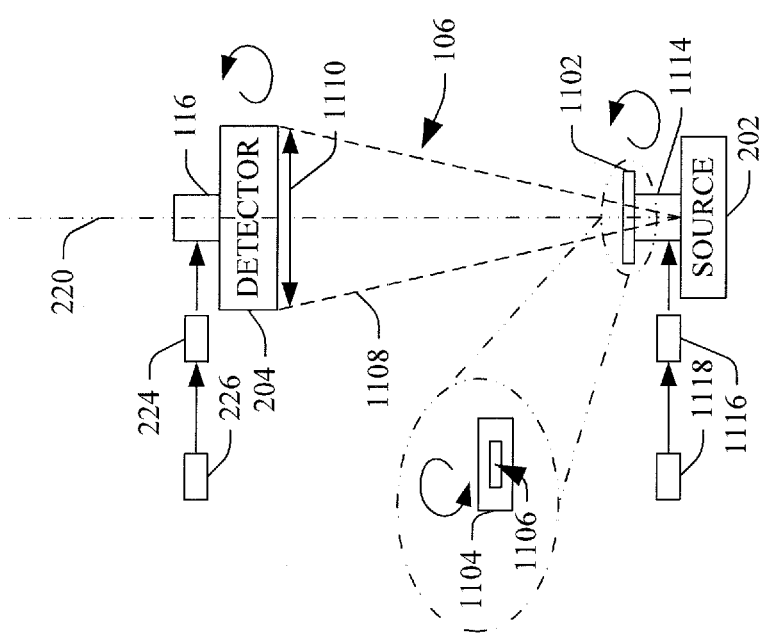

With the system of FIG. 2, and as can be seen in connection with FIGS. 3A, 3B and 3C, with the rotating line of detectors 302, different portions 304 and 306 of the radiation 212 traversing the scanning region 206 do not always illuminate the rotating detector 204, for example, based on the rotation angle of the line of detectors 302 at any given time, and thus does not contribute to the reconstructed images. FIGS. 11 and 12 illustrate an embodiment in which the system 200 additionally includes a source collimator 1102, which attenuates such radiation. As such, radiation not contributing image reconstruction can be filtered so that it does not irradiate the object being scanned.

More specifically, the collimator 1102 includes a radiation attenuating region 1104 and an opening or material free region 1106 located therein. A geometric shape of the material free region 1106 is such that a radiation beam 1108 traversing the scanning region 206 will have a width 1110 (FIG. 11) and a depth 1112 (FIG. 12) at the detector 204 that substantially matches a geometry of the radiation detection surface of the detector 204.

The collimator 1102 is affixed to a rotating member 1114 and is positioned such that the material free region 1106 is in substantial alignment with a long axis of the detector 204. A motor 1116 rotates the collimator 1102, and a controller 1118 drives the motor 1116 to rotate the collimator 1102 in coordination with a rotating detector 204 such that the material free region 1106 remains in substantial alignment with the long axis of the detector 204.

FIG. 11 shows the detector 204 and the collimator 1102 at a first angle, and FIG. 12 shows the detector 204 and the collimator 1102 at a second angle, which is about ninety degrees angularly offset from the first angle. As shown, the beam 1108 geometry tracks the geometry of the detector 204 as the detector 204 and the collimator 1102 rotate.

Figure 13:
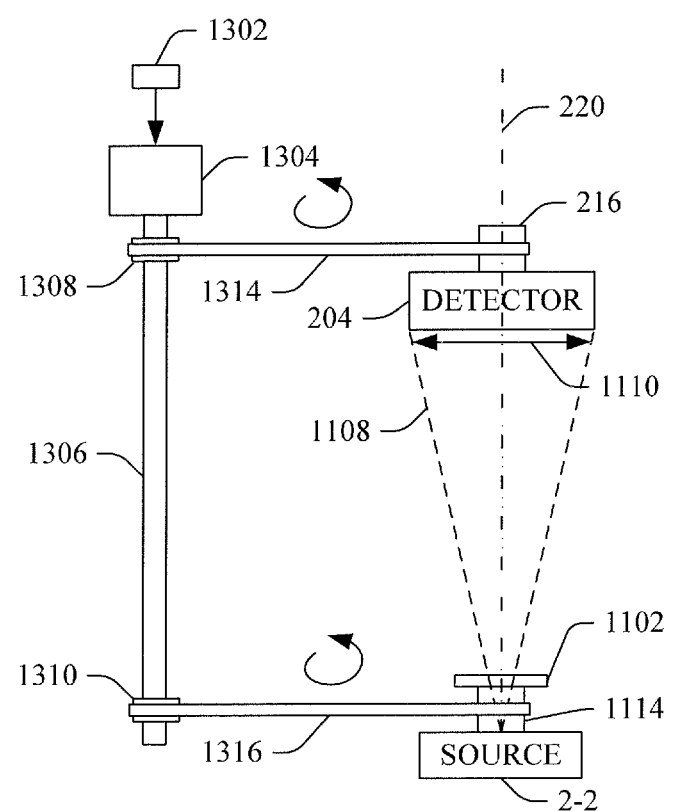

FIG. 13 shows an alternative embodiment in which a single controller 1302 controls a single motor 1304 to rotate a shaft 1306 and thus members 1308 and 1310 affixed thereto that respectively rotate belts or chains 1314 and 1316, which respectively rotate the rotating couplings 116 and 1114, which respectively rotate the detector 204 and the collimator 1102.

Figure 14:
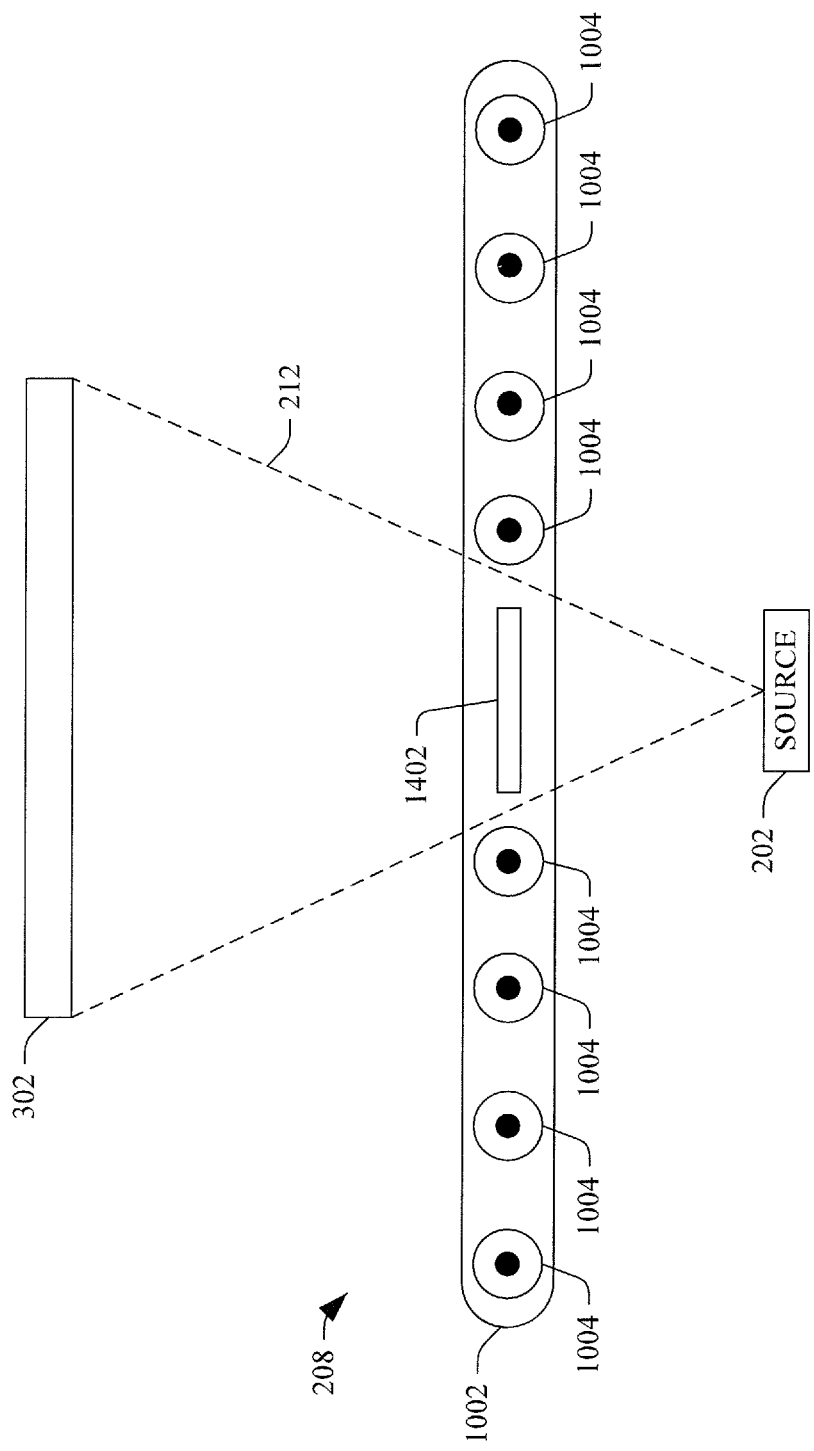
Figure 15:
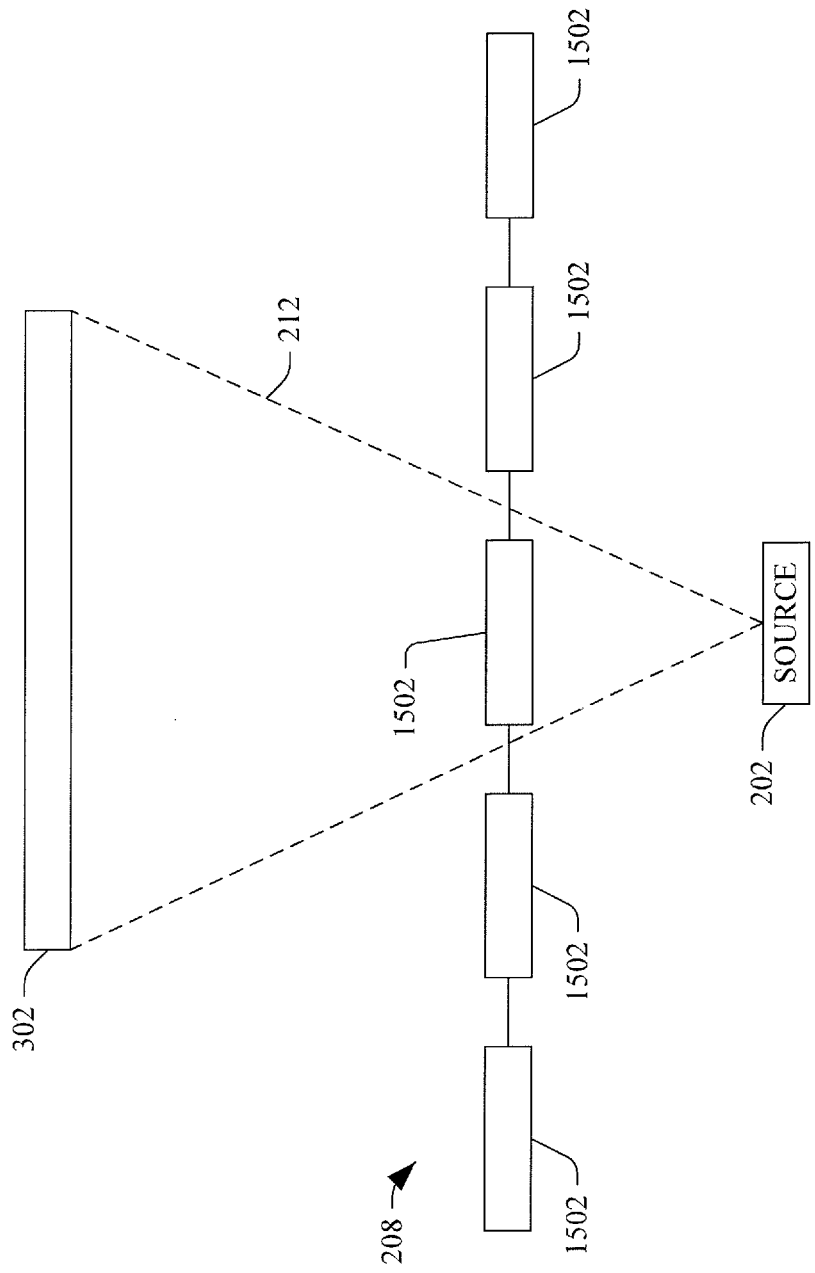

FIGS. 14 and 15 schematically illustrate alternate examples of the mover 208. FIG. 14 is substantially similar to the embodiment of FIG. 10, except that instead of the second set of rollers 1006, a radiation translucent support 1402 such as a carbon fiber plate or other radiation translucent support is used in the path of the radiation 212. In FIG. 15, the mover 208 includes a train of translucent trays 1502 rather than the belt 1002 and rollers 1004 and 1006. The mover 208 may also include a combination of the radiation translucent rollers, plate and trays, and/or other approach.

FIGS. 16, 17, 18, 19, 20, 21, 22, 23, 24, 25, 26 and 27 illustrate a set of non-limiting variations of the geometry of the line of detectors 302.

In FIG. 16, the line of detectors 302 includes a single row of detectors that extends from the rotation axis 220 in a single direction. Generally, the coverage in this configuration is about half of that in the configuration of FIG. 3A. This may also require less hardware, for example, half as many detectors of that of the configuration of FIG. 3A, given a same number of detectors modules in each branch extending from the rotation axis 220.

In FIG. 17, the line of detectors 302 includes two lines of detectors 1702 and 1704. In this embodiment, each of the lines of detectors 1702 and 1704 is linear and extends symmetrically about the rotation axis 220. In addition, the lines of detectors 1702 and 1704 are rotationally positioned with respect to each other angularly offset by about ninety degrees. In a variation, the line of detectors 302 includes more than two sub-lines of detectors. Additionally or alternatively, the angular offset between the sub-lines of detectors can be different.

In FIG. 18, the line of detectors 302 includes a first line of detector 1802, which is substantially similar to the line of detector of FIG. 3A. The line of detectors 302 also includes a plurality of other lines of detectors, including outer lines of detectors 1804 and intermediate lines of detectors 1806. Note that the terms "outer" and "intermediate" are only used here to indicate a relative position of the lines of detectors 1804 and 1806 with respect to the line of detector 1802. That is, the lines of detectors 1804 are parallel to the line of detector 1802, on opposing sides of the line of detector 1802, and in the plane facing the examination region 106, and the lines of detectors 1806 are between the line of detector 1802 and the lines of detectors 1804.

In FIG. 18, a length of the lines of detectors 1806 is smaller then a length of the line of detector 1802, and a length of the lines of detectors 1806 is smaller then the length of the lines of detector 1804, with the lines of detectors 1802-1806 extending from an outer region 1810 of the line of detector 2202 towards an inner region 1812 about the rotation axis 220. In other embodiments, the relative lengths may be different. Additionally or alternatively, the lines of detectors 302 may extend from the inner region 1812 towards the outer region 1810, as shown in FIG. 19. FIGS. 20 and 21 illustrate variations of FIGS. 18 and 19 that include two sets of the lines of detectors, located on opposite sides of the rotation axis 220.

FIG. 22 illustrates an embodiment in which the line of detectors 302 includes a center line of detectors 2202 that is substantially similar to that of the line of detector of FIG. 3A, except shorter, and branches 2204 that respectively extend from opposing end regions of the center line of detectors 2202. In this example, the second and third branches 2204 extend at angles α from the center line of detector 2202, with respect to the long axis of the center line of detectors 2202, which are greater than ninety degrees. In other embodiment, the branches 2204 may extend at smaller or larger angles.

FIG. 23 illustrates an embodiment in which the line of detectors 302 is arranged in a back-to-back "Y" configuration 2302. Other configurations such as a "T," an "L" or the like are also contemplated herein. FIG. 24 illustrate an embodiment in which the line of detectors 302 includes a linear support 2302 that supports a set of lines of detectors 2404, which are arranged parallel with respect to each other and angled with respect to the support 2402. FIG. 25 illustrates an embodiment in which the line of detectors 302 includes is two parallel lines of detector 2502, which are arranged symmetrically with respect to each other about the rotation axis 220, and supported by a support 2504.

FIG. 26 illustrates an embodiment in which the line of detectors 302 includes a curved line of detectors 2602, and FIG. 27 illustrates an embodiment in which the line of detectors 302 includes multiple linear segments 2702 connected to form a curved line of detectors. With these configurations, rotating the detector 204 will create a surface of detector elements. These configurations can be utilized as described herein.

It is to be appreciated that other geometries including combinations of one or more of the above are also contemplated herein.

FIG. 28 illustrates an embodiment in which the line of detectors 302 translates over the scanning region 206 to create a plane of detection. With this embodiment, the line of detectors 302 translates independent of the mover 208 and at a different speed. Although the line of detectors 302 is shown translating in a single direction, it is to be understood that the line of detectors 302 can translate in an apposing direction or, alternately, in both directions. With this embodiment, the hardware shown in FIG. 2 that rotates the line of detectors 302 is replaced with hardware for suitably translating the line of detectors 302.

FIG. 29 illustrates an embodiment in which the line of detectors 302 pivots over the scanning region 206 to create a plane of detection. Likewise, although the line of detectors 302 is shown pivoting in a single direction, it is to be understood that the line of detectors 302 can pivot in an apposing direction or, alternately, in both directions. Similarly, the hardware shown in FIG. 2 that rotates the line of detectors 302 can be replaced with hardware for suitably pivoting the line of detectors 302 with this embodiment. Such hardware may be substantially similar in that it include a stationary portion and rotating or pivoting portion.

It is to be appreciated that in another embodiment, the line of detectors 302 can move through a combination of one or more of rotating (FIG. 3A), translating (FIG. 28), pivoting (FIG. 29) and/or other movement to create the plane of detection.

FIG. 30 illustrates an embodiment which includes two lines of detectors 302 above the scanning region 206. In this example, each line of detectors 302 covers a sub-portion of the mover 208, and the line of detectors 302 do not cover overlapping regions of the mover 208. In addition, the lines of detectors 302 are offset along a long axis of the mover 208. Furthermore, the lines of detectors 302 have different lengths. Moreover, the lines of detectors 302 are shown rotating in the same direction.

In another embodiment, more than two lines of detectors 302 can be employed. In addition, at least two of the lines of detectors 302 can cover partial or the full mover 208, and partially or fully overlapping regions. Furthermore, the lines of detectors 302 do not have to be offset, and can have the same length. Furthermore, the lines of detectors 302 can rotate in opposite directions. Moreover, one or more additional sources 202 can be incorporated into the system.

FIG. 31 illustrates an embodiment which includes two lines of detectors 302, one above the scanning region 206 and one on the side of the region 306. Likewise, in another embodiment, the two lines of detectors 302 can be otherwise arranged, and more than two lines of detectors 302 can be utilized. Furthermore, one or more additional sources 202 can be incorporated into the system.

Other detector arrangements, including variants and/or combinations of the above and/or other arrangements are also contemplated herein.

Figure 32:
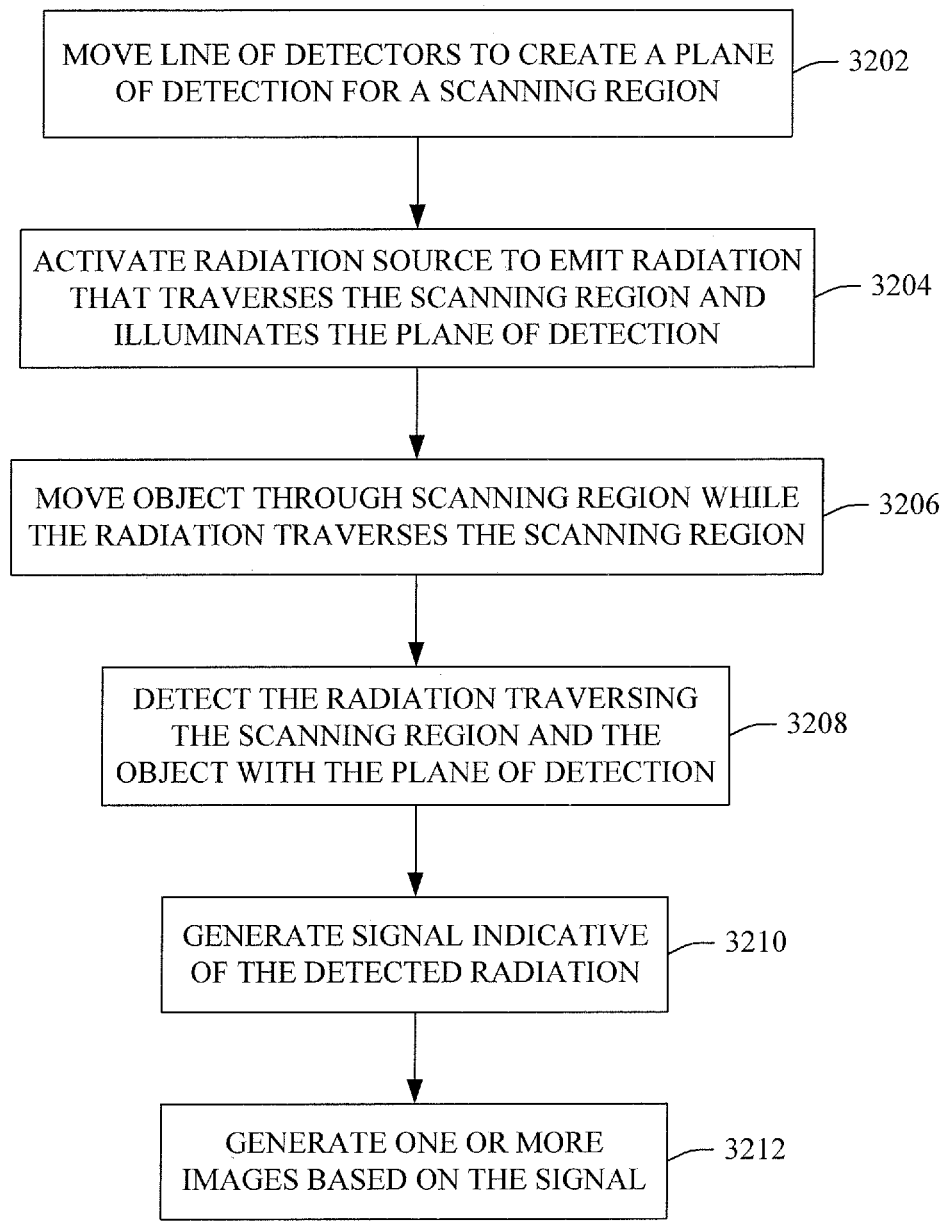
FIG. 32 schematically illustrates an example method.

FIG. 32 illustrates an example method for employing the imaging system 200.

It is to be understood that the following acts are provided for explanatory purposes and are not limiting. As such, one or more of the acts may be omitted, one or more acts may be added, one or more acts may occur in a different order (including simultaneously with another act), etc.

At 3202, a line of detectors is moved to create a plane of detection for scanning an object in the scanning region. As described herein, the line of detectors can be rotated, translated, pivoted and/or otherwise moved parallel to the scanning region to create the plane of detection.

At 3204, a radiation source is activated to emit radiation that traverses the scanning region and illuminates the plane of detection.

At 3206, a mover moves an object through the scanning region while the radiation traverses the scanning region;

At 3208, radiation traversing the scanning region and the object is detected with the plane of detection. As described herein, each voxel in the scanning region is sampled from multiple angles.

At 3210, a signal indicative of the detected radiation is generated.

At 3212, the signal is processed to generate one or more images. As described herein, the signal can be processed to generate two and/or three dimensional data indicative of the object.

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more computer readable instructions are carried by transitory medium such as a signal or carrier wave.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A scanner, comprising:
   a radiation source that emits radiation that traverses a scanning region;
   a detector array, including a line of detectors, that detects radiation traversing the scanning region, wherein the radiation source is located on a first side of the scanning region and the line of detectors is located on a second opposing sides of the scanning region, and the first and second sides face each other; and
   a mover configured to move an object through the scanning region when scanning the object,
   wherein the line of detectors is configured to rotate in a plane, which is parallel to the second side of the scanning region, in coordination with the mover moving the object, thereby creating a plane of detection for scanning the object.

2. The scanner of claim 1, wherein the line of detectors is configured to translate in the plane to create the plane of detection.

3. The scanner of claim 1, wherein the line of detectors rotates at a speed such that a voxel representing a sub-region of the object is scanned from multiple different angles as the object moves through the scanning region.

4. The scanner of claim 1, wherein the line of detectors is a single row of detector elements.

5. The scanner of claim 1, wherein a detection area of the detection plane is larger than a detection area of the line of detectors.

6. The scanner of claim 1, further comprising:
   a coupling, including a stationary portion and a rotating portion, wherein the detector array is affixed to and rotates in coordination with the rotating portion;
   a motor configured to rotate the rotating portion; and
   a controller that controls the motor to rotate the rotating portion.

7. The scanner of claim 1, the mover, comprising:
   a conveyor belt; and
   a plurality of rollers configured to move the conveyor belt, wherein a portion of the conveyor belt in the scanning region includes support structure of at least one of a set of radio-translucent rollers or a radio-translucent support plate.

8. The scanner of claim 1, the mover, comprising:
   a train of radio-translucent trays.

9. The scanner of claim 1, further comprising:
   a source collimator located between the source and the scanning region, wherein the source collimator is configured to collimate the emitted radiation so that a geometry of the radiation incident on the line of detectors substantially matches a geometry of a radiation sensitive region of the line of detectors, and the source collimator is moved in coordination with the moving line of detectors so that the radiation remains incident on the line of detectors as the line of detectors moves.

10. The scanner of claim 1, further comprising:
    at least a second detector array that detects the radiation traversing the scanning region.

11. The scanner of claim 1, wherein the object is luggage, and the scanner is an airport security scanner.

12. A method for scanning an object in a scanning region, comprising:
    pivoting a line of detectors to create a plane of detection for scanning the object in the scanning region;
    moving the object through the scanning region;
    producing radiation that traverses the scanning region and the object moving there through; and
    detecting the radiation traversing the scanning region and the object with the plane of detection and generating a signal indicative thereof.

13. The method of claim 12, wherein the line of detectors is configured to translate in the plane to create the plane of detection.

14. The method of claim 12, further comprising:
    moving the line of detectors rotates at a speed such that a voxel representing a sub-region of the object is scanned from at least two different angles as the object moves through the scanning region.

15. The method of claim 12, further comprising:
    generating two dimensional images of the object based on the signal.

16. The method of claim 15, further comprising:
    performing, before generating the two dimensional images of the object based on the signal, at least one correction to the signal.

17. The method of claim 16, wherein the at least one correction includes at least one of a detector sensor offset correction, a detector sensor gain correction, a detector sensor linearity correction or a detector sensor spectral response correction.

18. The method of claim 15, further comprising:
    filtering, before generating the two dimensional images of the object based on the signal, using a ramp-shaped filter kernel that emphasizes high frequencies.

19. The method of claim 15, further comprising:
    weighting, before generating the two dimensional images of the object based on the signal, the signal based on a distance from a center of the line of detectors.

20. The method of claim 15, further comprising:
    varying a detection sampling rate based on a distance from a center of the line of detectors.

21. The method of claim 15, wherein the two dimensional images of the object are generated based on an iterative reconstruction algorithm.

22. The method of claim 15, wherein the two dimensional images includes a series of contiguous or partially overlapping images, and generating three dimensional data of the object based on the series of images.

23. Computer readable storage medium with computer executable instructions embedded thereon, which, when executed by a processor, cause the processor to:
- one of rotate or pivot a line of detectors parallel to a side of a scanning region so as to create a plane of detection for scanning an object in the scanning region;
- move a mover which moves the object through the scanning region;
- activate a source to produce radiation that traverses the scanning region and the object moving there through;
- activate the line of detectors to detect the radiation traversing the scanning region and the object with the plane of detection and generate a signal indicative thereof; and
- generate three dimensional data of the object, including an interior of the object, based on the signal.

\* \* \* \* \*